United States Patent
Toleti et al.

(10) Patent No.: US 8,284,024 B2
(45) Date of Patent: Oct. 9, 2012

(54) SYSTEM AND METHOD OF ISSUING PATIENT IDENTIFICATION DEVICES

(75) Inventors: Chakravarthy S. Toleti, Windermere, FL (US); Rajesh S. Toleti, Windermere, FL (US); Nageshwara R. Vempaty, Saratoga, CA (US)

(73) Assignee: QuadraMed Affinity Corporation, Reston, VA (US)

( * ) Notice: Subject to any disclaimer, the term of this patent is extended or adjusted under 35 U.S.C. 154(b) by 566 days.

(21) Appl. No.: 12/432,979

(22) Filed: Apr. 30, 2009

(65) Prior Publication Data

US 2010/0277274 A1    Nov. 4, 2010

(51) Int. Cl.
*G06F 7/04* (2006.01)
(52) U.S. Cl. .............................. 340/5.8; 340/5.52; 705/3
(58) Field of Classification Search ............... 340/10.42, 340/10.4, 1.1, 539.12, 10.1
See application file for complete search history.

(56) References Cited

U.S. PATENT DOCUMENTS

| | | | |
|---|---|---|---|
| 2004/0099731 A1* | 5/2004 | Olenick et al. | 235/380 |
| 2007/0258626 A1* | 11/2007 | Reiner | 382/115 |
| 2008/0121699 A1* | 5/2008 | Thorsen et al. | 235/381 |
| 2009/0006439 A1* | 1/2009 | Joseph et al. | 707/102 |
| 2009/0164680 A1* | 6/2009 | Stobbe et al. | 710/110 |
| 2009/0281825 A1* | 11/2009 | Larsen | 705/2 |

* cited by examiner

*Primary Examiner* — Brian Zimmerman
*Assistant Examiner* — Sara Samson
(74) *Attorney, Agent, or Firm* — Crowell & Moring LLP

(57) ABSTRACT

A system and method of issuing patient identification devices to patients in a self service fashion at a provider facility. The system includes a processor for obtaining first patient identification information from a patient, for retrieving second patient identification information from patient records, for positively identifying the patient by comparing the first identification information to the second identification information, for initiating a patient identification device with a code unique to the patient, for issuing the identification device to the patient, and for storing an indication that the identification device has been initiated and issued.

20 Claims, 2 Drawing Sheets

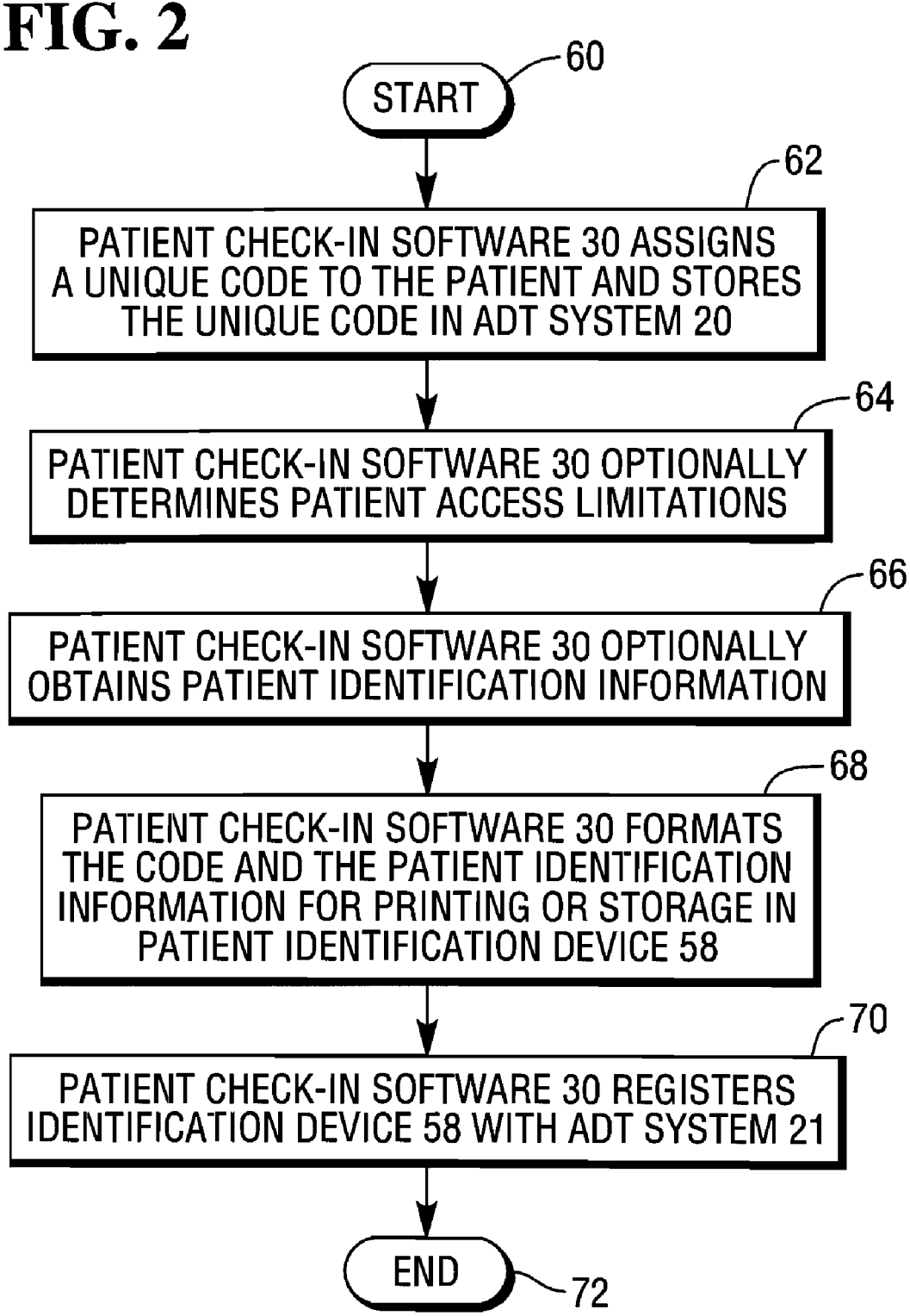

SYSTEM AND METHOD OF ISSUING PATIENT IDENTIFICATION DEVICES

BACKGROUND

Patients go to health care providers for treatment of health problems. Health care providers include physicians, technicians, and other healthcare personnel and the offices they work in, including offices, clinics, and hospitals. A patient visit to a provider is known as an encounter.

Patients typically check in at a reception or front desk. Front desk personnel issue devices or tokens that identify the patients for the duration of their encounters. Patients may become dissatisfied with long lines at the front desk, especially those who are sick or uncomfortable.

It would be desirable to provide a system and method of issuing patient identification devices that overcomes these problems.

SUMMARY

A system and method of issuing patient identification devices is provided.

The system includes a processor for obtaining first patient identification information from a patient, for retrieving second patient identification information from patient records, for positively identifying the patient by comparing the first identification information to the second identification information, for initiating a patient identification device with a code unique to the patient, for issuing the identification device to the patient, and for storing an indication that the identification device has been initiated and issued.

BRIEF DESCRIPTION OF THE DRAWINGS

FIG. 2 is a flow chart illustrating a method of issuing a patient identification device.

DETAILED DESCRIPTION

Figure 1:
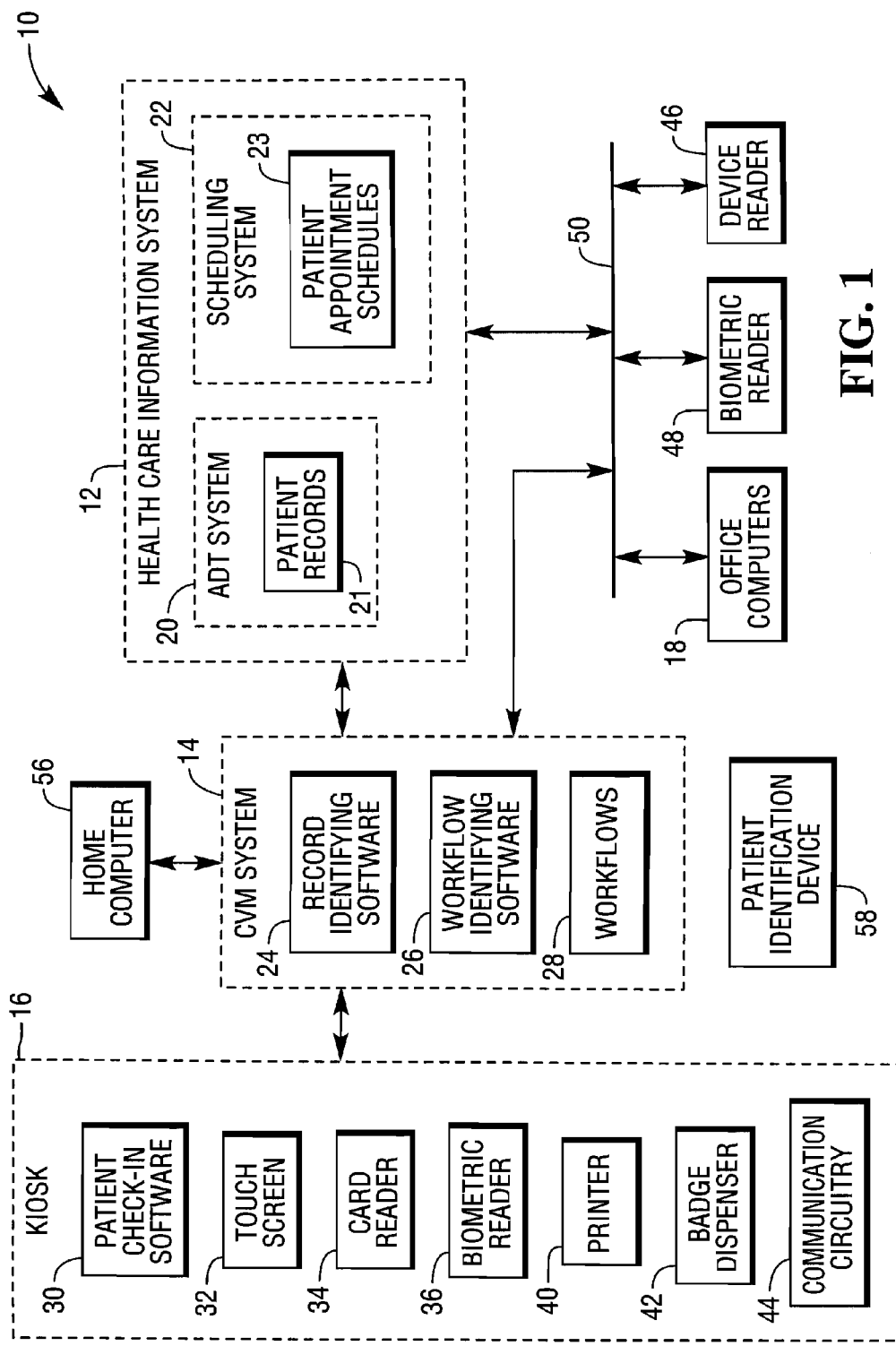
FIG. 1 is a block diagram of a healthcare system.

With reference to FIGS. 1 and 2, healthcare system 10 includes healthcare information system 12, customer value management (CVM) system 14, and one or more kiosks 16. Healthcare information system 12, CVM system 14, and kiosk 16 include computers with processors and memory for executing programs and storing data. Healthcare information system 12 and CVM system 14 may be combined into a single computer. One or more of the systems may be combined with other information systems or may be absent based on specific circumstances.

Healthcare system 10 may be located at a healthcare provider office. The healthcare provider office may include a front desk, a lounge, and examination rooms.

Kiosk 16 may be located in the lounge, or near an entrance to the healthcare provider office, for completing patient check-in. CVM system 14 may also be located at the healthcare provider office. Healthcare information system 12 may be located at the healthcare provider office or may be external to the healthcare provider office. Healthcare system 10 may include office computers 18 at the front desk and in examination rooms.

Healthcare information system 12, customer value management CVM system 14, kiosk 16, and office computers 18 may all be connected via a network 50. If healthcare information system 12 is located externally, CVM system 14 may alternatively access healthcare information system 12 using several methods, including one or more network protocols, and optionally higher level protocols for messaging and file transfer. A common standard for exchanging healthcare data between health care information systems is HL7. CVM system 14 can receive patient information and schedule information via messages formatted in HL7 from health care information system 12. Alternatively, it can receive patient information via a flat file in a comma separated value (CSV) format.

The healthcare provider office may impose various security measures in and around healthcare information system 12, CVM system 14, kiosk 16, office computers 18, and network connections between healthcare information system 12, CVM system 14, kiosk 16, and office computers 18. For example, healthcare system 10 may rely on role based access control in conjunction with Secure Sockets Layer (SSL) protocol for secure data transmission. Role based access control ensures that a user is associated with a role or a plurality of roles and only the authorized information for the role(s) is displayed to the specific user. The SSL protocol encrypts network packets of information during transport to deter eavesdropping. People or applications listening to packets in transmission get encrypted data which is hard to decipher. The combination of role based access control and information encryption typically provides secure access to data.

Healthcare information system 12 stores patient information. Healthcare information system 12 may include admission, discharge, and transfer (ADT) system 20 and scheduling system 22. ADT system 20 and scheduling system 22 may include one or more servers.

ADT system 20 includes patient records 21, which include patient identification information, such as name, phone number, date of birth. Patient records 21 may further include a photograph and biometric information. ADT system 20 provides patient identification information to kiosk 16 during patient check-in.

ADT system 20 also records initiation and issuance of patient identification devices 58 to patients during check-in. ADT system 20 further logs use of patient identification devices 58, including areas visited in a healthcare facility. ADT system 20 may initiate patient identification devices 58 with security privileges which limit patient access to certain areas of the healthcare facility. Finally, ADT system 20 may initiate patient identification devices 58 with purchasing power and track patient spending.

Patient identification devices 58 may include identification tokens, identification badges, patient held appliances, such as patient cell phones or pagers, and other identification devices.

Scheduling system 22 includes patient appointment schedules 23.

CVM system 14 executes record identifying software 24 which attempts to match patient records 21 to patient identifying information presented by patients during checking in. Record identifying software 24 performs the matching process in a way that is compliant with a local security policy.

The local security policy typically complies with the Health Insurance Portability and Accountability Act of 1996 (HIPAA). It addresses security issues associated with authentication of patients, authorization to access patient information, and auditing of access to information. The local security policy may require that certain types of identifying information be presented by a patient during a visit to a healthcare provider office, and that a potential match between the information presented by the patient and information in patient records in healthcare information system 20 satisfy a minimum confidence level. The security policy can be defined at any level, including specific documents, forms, specific elements of a document/form, and can be specialized for the type of access, including viewing, creating, updating, deleting, and versioning.

In an example local security policy, a patient may be required to provide his/her name, phone number, and date of birth. Record identifying software 24 uses this information to find a corresponding patient record 21 in CVM system 14. For example, record identifying software 24 may complete the following procedure:

1. Obtain a name and telephone number from the patient at kiosk 16.
2. Compare the name and phone number presented in step 1 to patient information stored in ADT system 20 to produce a list of potential matches between the presented name and telephone number and the patient information stored in records 21.
3. Obtain the patient's date of birth at kiosk 16.
4. For each potential match on the list of step 2, eliminating those potential matches not having the same date of birth entered in step 3 in records 21 and not having an appointment during the current time period of interest. (The interval of tolerance for the match can be custom defined, for example it can be one day).

Other techniques for matching patient records 21, as well as other combinations of these same techniques, are also envisioned. For example, further identification credentials, such as an identity number, identity card, or a biometric, such as a fingerprint, can be added to the process above as additional identification credentials. They can be used in addition to, or in place of, other identification credentials, as dictated by the local security policy. They can be added based on specific security policies or specific needs of health care providers such as surgical procedures. For example, a cataract surgery may require three factors of identification and in addition may ask the patient to identify whether they are present for a cataract operation in the left eye or the right eye.

CVM system 14 additionally executes workflow identifying software 26 which examines the appointment schedule 23 of the patient in scheduling system 22. Workflow 28 may present the patient with requests for information and present questions or guidance based upon the answers. For a walk-in, workflow identifying software 26 examines the purpose of the visit entered by the patient and identifies a workflow 28 based on the purpose.

Kiosk 16 includes touch screen 32. Kiosk 16 may include additional peripherals for recording patient identifying information in order to satisfy the local security policy, such as card reader 34 for reading patient identification cards and a biometric reader 36, such as a fingerprint reader, for capturing biometric information.

Kiosk 16 executes patient check-in software 30 which displays prompts instructing patients to enter their identifying information, in accordance with the local security policy, and which passes the identifying information to record identifying software 24 for analysis and authentication.

If record identifying software 24 cannot reduce the list of potential matches to a unique match (i.e., if the list contains more than one potential match or no potential matches, or if the confidence level associated with a potential unique match does not meet the local security policy in effect, or if the patient is unable to provide sufficient identification information), kiosk 16 displays a message instructing the patient to seek manual processing at the front desk. Office employees at the front desk may access patient records 21 in healthcare information system 12 through any of office computers 18. They can utilize the patient identification information obtained at the kiosk thus far or may start afresh.

If record identifying software 24 is able to produce a unique match, patient check-in software 30 engages workflow identifying software 26 to find a workflow 28 related to the reason for the patient's visit. If workflow identifying software 26 identifies a workflow 28, patient check-in software 30 executes that workflow 28. Workflow 28 presents the patient with forms, guidance and questions, and processes answers to the questions.

Patient check-in software 30 may be a web application. The patient accesses and enters information through a web browser executed by kiosk 16 or a home computer 56. Patients may update their information, i.e., read and write information, securely through patient check-in software 30. Patient information may be encrypted to make it secure for sending over the network 50.

Patient check-in software 30 additionally initiates patient identification devices 58. Patient check-in software 30 retrieves identifying information to be included in identification device 58 from ADT system 21 and registers identification device 58 in patient records 21. Patient check-in software 30 may additionally initiate patient identification devices 58 with other information, such as arrival time, wait time, or monetary stored value information as a purchasing device.

For example, kiosk 16 may include printer 40 for printed patient identification papers, device dispenser 42 for patient identification cards, or communication circuitry 44 for wired or wireless patient identification devices 58.

If the healthcare facility uses printed patient identification papers, patient check-in software 30 at kiosk 16 or home computer 56 may print patient identification papers in a variety of formats using printer 40. For example, patient identification papers may include one or more characters of text, a patient photograph, and a patient barcode containing a unique code linked to patient identification information in ADT system 21.

If the healthcare facility uses patient identification cards, patient check-in software 30 may produce patient identification cards or badges in a variety of formats using device dispenser 42. For example, identification device 58 may include a radio frequency identification (RFID) tag, a barcode, a magnetic stripe, contact or contactless memory chip, near field communication (NFC) capable device, or other type of data storage containing patient identification information or a unique code. Identification device 58 may additionally include identifying text information and/or photographic information.

If the healthcare facility uses a wireless communication device, such as a patient cell phone, patient check-in software 30 may store a unique code in the cell phone memory via communication circuitry 44. Alternately or in addition to this, patient check-in software 30 may register the unique identification code of the cell phone, such as phone number or subscriber identity module (SIM) card identification number or a near field communication (NFC) identification number or a combination there of, in its database or in other back end systems.

A healthcare provider may identify patients from their identification devices 58. Office computers 18 and entrances to secure areas include corresponding readers 46, which may include RFID tag readers, barcode readers, magnetic stripe reader, contact or contactless memory chip reader, or NFC readers. Office computers 18 and entrances to secure areas may optionally include biometric readers 48 as well. Further patient identification during the visit can utilize the patient identification device issued in addition to or in lieu of other patient identification credentials such as patient name, finger print, photo, drivers license, etc.

Patient check-in software 30 may register patient identification device 58 for multiple visits. Patient check-in software 30 may in addition be customized to deprovision the patient identification device 58 from patient records 21 at the end of the encounter. A healthcare provider may optionally choose to deprovision, collect or destroy identification devices 58 when patients leave the healthcare provider's facility.

In an example encounter, a patient visiting a healthcare provider office has an appointment. The patient walks up to kiosk 16. Kiosk 16 executes patient check-in software 30 to obtain patient identifying information. Patient check-in software 30 interacts with record identifying software 24 of CVM system 14 to complete the patient record identification procedure. Record identifying software 24 positively identifies the patient record in healthcare information system 12 and returns information to be included in patient identification device 58. Patient check-in software 30 initiates patient identification device 58, by printing, dispensing, communicating or by other means with patient identification device 58.

Patient check-in software 30 interacts with workflow identifying software 26 to look up the details of the patient's appointment in the patient's record. For example, workflow identifying software 26 may determine that the appointment is for a blood sugar test and determine a corresponding workflow 28 for the blood sugar test. Patient check-in software 30 then executes the workflow 28.

With reference to FIG. 2, an example method of initiating and issuing a patient identification device 58 is illustrated beginning with START 60.

In step 62, patient check-in software 30 identifies and assigns a unique code to a patient identification device 58. Patient check-in software 30 may additionally display helpful information explaining the purpose of identification device 58, how to use it, and how to return it.

In step 64, patient check-in software 30 optionally determines patient access limitations. Patient check-in software 30 may display these limitations to the patient. ADT system 20 monitors patient movements and permits or denies access to secured areas based upon the access limitations assigned to the patient's code.

In step 66, patient check-in software 30 optionally retrieves patient identification information from ADT system 21.

In step 68, patient check-in software 30 formats the code and sends the formatted information for printing and/or storage in patient identification device 58.

For example, patient check-in software 30 may send the formatted information to printer 40 and cause printer 40 to print an identification paper with a barcode containing the issued patient identification code for the encounter.

As another example, patient check-in software 30 may send the formatted information to badge dispenser 42 and cause badge dispenser 42 to print and/or store the formatted information in or on an identification card or badge. The code may be contained with a printed barcode or stored within an RFID tag, magnetic stripe, or other storage mechanism within the card.

As another example, patient check-in software 30 may send the formatted information to a patient held device, such as a cell phone.

In step 70, patient check-in software 30 registers patient identification device 58 with ADT system 21. When a patient leaves, patient check-in software 30 may unregister patient identification device 58 using any of office computers 18. The healthcare provider may require that patients return issued patient identification devices 58 at kiosk 16 or a drop off point near an exit. A patient held device such as a cell phone may be deprovisioned for identification capability a the end of an encounter.

Operation ends at step 72, when the identification device is issued to the patient.

Although particular reference has been made to certain embodiments, variations and modifications are also envisioned within the spirit and scope of the following claims.

What is claimed is:

1. A computer comprising:
a processor for obtaining first patient identification information from a patient, for retrieving second patient identification information from patient records, for positively identifying the patient by comparing the first identification information to the second identification information, for initiating a patient identification device with a code unique to the patient, for issuing the identification device to the patient, and for storing an indication that the identification device has been initiated and issued; wherein:
the processor positively identifies the patient based on a variable amount of first patient information, said variable amount being a function of a purpose of an encounter with the patient.

2. A system for issuing identification devices to patients comprising:
a provider of an identification device; and
a computer for obtaining first patient identification information from a patient, for retrieving second patient identification information from patient records, for positively identifying the patient by comparing the first identification information to the second identification information, for initiating the patient identification device, for causing the provider to issue the identification device to the patient, and for storing an indication that the identification device has been initiated and issued to the patient for an encounter; wherein:
the computer positively identifies the patient based on a variable amount of first patient information, said variable amount being a function of a purpose for the encounter.

3. The system of claim 2, wherein the kiosk initiates the identification device with a unique identifier.

4. The system of claim 3, wherein the kiosk initiates the identification device with an identifier including one or more of a name, a photograph, and a biometric.

5. The system of claim 3, wherein the kiosk initiates the identification device with an identifier unique to the patient.

6. The system of claim 3, wherein the kiosk initiates the identification device with an identifier unique to the encounter.

7. The system of claim 3, wherein the kiosk initiates the identification device with an identifier unique to the encounter and a number of additional encounters.

8. The system of claim 3, wherein the unique identifier is represented as a barcode.

9. The system of claim 3, wherein the identification device is a radio frequency identification tag and wherein the unique identifier is stored in the radio frequency identification tag.

10. The system of claim 3, wherein the identification device is a badge including the unique identifier.

11. The system of claim 3, wherein the identification device is a near field communications device and the unique identifier is stored in the near field communications device.

12. The system of claim 11, wherein the near field communications device comprises a patient cellular telephone.

13. The system of claim 2, wherein the computer comprises a kiosk at a healthcare provider facility.

14. The system of claim 2, wherein the computer comprises a personal computer remote from a healthcare provider facility.

15. The system of claim 3, wherein the provider comprises a printer and the identification device is a paper printed with the unique identifier.

16. The system of claim 3, wherein the provider comprises a printer and the identification device is a patient badge printed with the unique identifier.

17. The system of claim 3, further comprising a security system for controlling patient access to areas of a healthcare facility based upon the unique identifier, wherein the computer sends the identifier to the security system.

18. The system of claim 7, wherein the security system maintains a log including the unique identifier and usage of the unique identifier by the patient.

19. The system of claim 3, further comprising a receptacle for storing the patient identification device received from the patient after the encounter has ended.

20. The system of claim 3, wherein the computer deprovisions the patient identification device after the encounter has ended.

* * * * *